United States Patent [19]

della Valle et al.

[11] Patent Number: 5,190,925
[45] Date of Patent: Mar. 2, 1993

[54] USE OF GANGLIOSIDES IN THE TREATMENT OF AUTONOMIC DYSFUNCTION IN CHAGAS' DISEASE

[75] Inventors: Francesco della Valle, Padova, Italy; Daniel J. Iosa, Cordoba, Argentina

[73] Assignee: Fidia, S.p.A., Abano Terme, Italy

[21] Appl. No.: 829,598

[22] Filed: Feb. 3, 1992

Related U.S. Application Data

[63] Continuation of Ser. No. 446,108, Dec. 5, 1989, abandoned.

[30] Foreign Application Priority Data

Jun. 8, 1989 [IT] Italy ................ 48063 A/89

[51] Int. Cl.$^5$ ............................................. A61K 31/70
[52] U.S. Cl. .................................... 514/25; 514/54; 514/62
[58] Field of Search ........................... 514/25, 54, 62

[56] References Cited

U.S. PATENT DOCUMENTS 4,347,244 8/1982 Mynard et al. ............... 514/25
4,710,490 12/1987 Catsimpoolas et al. ........ 514/25
4,940,694 7/1990 Della Valle et al. ........... 514/25

OTHER PUBLICATIONS

Tettamanti et al., Biochim. Biopays, Acta 296:160–170 (1973).
Micell et al.; ACTA Psychiat. Scand. 55:102–110 (1977).
Gorio et al.; Brain Research 197:236–241 (1980).
Svennerholm et al.; Biochim. Biophys. ACTA 617:97–109 (1980).
Nilsson et al.; J. Lipid Research 23:327–334 (1982).
Samson; Drugs of Today 22(2):73–107 (1986).
*The Merck Manual;* 15 Med. pp. 210–211 (1987).
Swindell et al.; Ophthalmic Res. 20:232–236 (1988).
Dialog Information Services, File 155 (Medline), Accession No. 06612231, F. Tessari et al., J. Diabetic Complications Jan.-Mar. 1988, 2(1) pp. 34–37.
K. J. Isselbacher et al., "Harrison's Principles of Internal Medicine", 9th Ed. 1980, pp. 878, 879.
Biochemical and Biophysical Research Communications, vol. 107, No. 3, Aug. 16, 1982, pp. 869–877, Zumbuhl et al.

*Primary Examiner*—Ronald W. Griffin
*Assistant Examiner*—Nancy S. Carson
*Attorney, Agent, or Firm*—Birch, Stewart, Kolasch & Birch

[57] ABSTRACT

A method and pharmaceutical composition are provided for the treatment of autonomic nervous system abnormalities caused by Chagas' diseases by the administration of gangliodises, particularly a mixture of ganliosides $GM_1$, $GD_{1a}$, $GD_{1b}$, and $GT_{1b}$.

10 Claims, No Drawings

USE OF GANGLIOSIDES IN THE TREATMENT OF AUTONOMIC DYSFUNCTION IN CHAGAS' DISEASE

This application is a continuation of application Ser. No. 07/446,108 filed Dec. 5, 1989, now abandoned.

BACKGROUND AND FIELD OF THE INVENTION

The present invention relates to the use of gangliosides, particularly a mixture of gangliosides, to treat autonomic nervous system abnormalities caused by Chagas' disease or American trypanosomiasis.

Chagas' disease or American trypanosomiasis is the most common cause of congestive heart failure and sudden death in the world and represents a major public health problem in Latin America. *Trypanosoma cruzi*, the etiologic agent of Chagas' disease, and its insect vectors have an extensive geographic distribution encompassing South and Central America, and extending to the southwestern and southeastern United States. The majority of patients, 90 to 95 percent, survive the acute phase of the illness which usually occurs in childhood. These patients then enter into a latent phase of the disease in which there are no clinical signs or symptoms related to *T. cruzi* infection. All patients exhibit positive serologic tests for *T. cruzi*. Recently, advanced cardiologic techniques have demonstrated subtle and potentially progressive functional and morphologic cardiac abnormalities in this phase of Chagas' disease Electrocardiographic studies have shown conduction system abnormalities and echocardiographic studies have documented impaired left ventricular function in asymptomatic patients Histopathologic studies using endomyocardial biopsies or tissues from chagasic patients who died of causes other than Chagas' disease have documented inflammatory lesions, fibrosis and degenerative changes of the myocardium. These findings have led many investigators to believe that a smouldering, slowly progressive destruction of the myocardium occurs in the latent phase which results in the severe myocardial pathology seen in the chronic phase of Chagas' disease Approximately 20 to 30 percent of *T. cruzi* infected patients progress to the chronic phase of Chagas' disease which is manifested by signs and symptoms of congestive heart failure and cardiac arrhythmias. The majority of patients are from 30 to 50 years of age and complain of symptoms consistent with congestive heart failure. Physical examination reveals signs of both right and left sided congestive heart failure. Electrocardiograms (ECG) typically show conduction defects, most notably right bundle branch block and/or left anterior hemiblock. Arrhythmias are commonly noted. Chest x-rays (CXR) reveal moderate to severe cardiomegaly. Once the onset of congestive heart failure is noted, the use of cardiotonic drugs, diuretics, or the implantation of pacemakers have been ultimately to no avail. Patients inexorably deteriorate with a mortality rate of greater than 90% within 5 years of the onset of cardiac symptoms. Pathologic examination of the hearts of patients who died from chronic Chagas' disease shows a markedly enlarged heart with dilation of all 4 chambers and areas of focal inflammation with myofiber destruction and fibrosis are evident.

Histopathologic examination of hearts from patients who died of chronic Chagas' disease sometimes reveals neuronal lesions. Reports have described the destruction of parasympathetic ganglia and their subsequent fibrosis in both the presence and absence of inflammatory cells, and have showed mononuclear cell lesions with interrupted and broken axis cylinders and perineuronal inflammation in chronic chagasic hearts, including neuronophagia of intracardiac ganglioneurons. Not surprisingly, patients with Chagas disease often show autonomic nervous system dysfunction. Reports have also documented abnormal responses to postural changes using the Valsalva maneuver exercise-related heart rate response; and infusion of pharmacologic agents such as atropine or Beta-blockers. The abnormal responses were noted in asymptomatic chagasic patients as well as in chagasic patients with signs or symptoms of congestive heart failure. Other investigators have reported similar findings, and have shown abnormal baroreceptor responses to phenylephrine administration, Valsalva maneuver, or hyperventilation testing.

The etiology of the neuronal lesions and autonomic nervous system dysfunction in Chagas' disease is unclear. Several theories have been proposed to explain these observations. It has been postulated that *T. cruzi* produces a neurotoxin that preferentially destroys the sympathetic nervous system and the parasympathetic nervous system of the heart. Some have reported the presence of a circulating antibody in the sera of patients with Chagas' disease that binds to nerve cells and have hypothesized that the neuronal lesions are autoimmune in nature. Unfortunately, to date, no good experimental or clinical evidence exists to establish the pathogenesis of the neuronal lesions seen in Chagas' disease.

The severe complications and widespread occurrence of Chagas' disease present a great need for a method to treat the disease and prevent its effects. It is this great need which is addressed and met by the present invention.

OBJECTS AND SUMMARY OF THE INVENTION

It is an object of the invention to provide a method to ameliorate and otherwise treat the neuronal destruction and autonomic nervous system dysfunction in Chagas' disease or American trypanosomiasis.

It is a further object of the invention to provide a method to induce neuronal regeneration, promote neuronal repair and facilitate normalization of autonomic nervous system functions in Chagas' disease patients.

These and other objects of the invention are accomplished by administering to Chagas' patients a therapeutically effective amount of gangliosides, particularly a mixture of gangliosides.

DETAILED DESCRIPTION OF THE INVENTION

Gangliosides represent a family of naturally occurring complex glycolipid molecules found in cellular membranes which have been shown to possess a reinnervation-stimulating activity due to enhanced nerve sprouting both in vitro and in vivo.

Exogenously applied gangliosides will insert into neuronal membranes in a stable manner. This incorporation is associated with the activation of a membrane-bound enzyme system, $(Na^+, K^+)$ ATPase whose activity is essential for nerve impulse conductivity. Ganglioside preparations have been shown to possess a reinnervation-stimulating activity due to enhanced nerve sprouting, an essential feature of muscular reinnervation processes and of restoration of synaptic contacts. Electrophysiological and functional evidence of early recovery, due to parenteral ganglioside treatment, from nerve damage has been obtained in several animal models, including sensory nerve function after nerve transection, cochlear impairment by noise, diabetic neuropathy in mutant diabetic mice and intoxication with neurotoxins.

Animal studies have shown electrophysiochemical and functional evidence of accelerated recovery from nerve damage due to trauma, toxins or metabolic derangements after treatment with gangliosides. Clinical trials of ganglioside therapy in patients with peripheral neuropathy resulting from diabetes, uremia/chronic renal failure, alcoholism, or mechanical/traumatic reasons have demonstrated effective improvement in recovery of function as compared to non-treated control patients. No untoward toxicity has been associated with ganglioside therapy in over 10 years of clinical trials.

Gangliosides are acidic glycolipids belonging to the family of biological compounds called glycosphingolipids. They are composed of 4 basic structural units: a long-chain aminoalcohol, a fatty acid, an oligosaccharide moiety and one or more sialosyl residues.

1. The long-chain aminoalcohol, present in brain gangliosides is identified as 4-sphingenine and its longer-chain analog as 4-eicosasphingenine; these compounds are commonly called sphingosines.

FIG. 1: Structures of Sphingosines

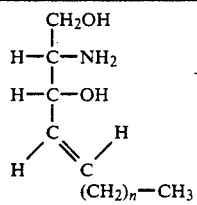

n = 12 4-spingenine
n = 14 4-eicosasphingenine

The corresponding saturated compounds (sphinganines) are also present in gangliosides in minor proportions.

2. A fatty acid is linked by means of an amide bond to the sphingosine base. In brain gangliosides this fatty acid is more than 95% accounted for by stearic acid (18:0). Other fatty acids are encountered in minor proportions, i.e. arachidic acid (20:0), palmitic acid (16:0) or palmitoleic acid (16:1Δ$^9$). The aminoalcohol plus the fatty acid form the unit termed ceramide, which represents the hydrophobic part of the ganglioside molecule.

3. The oligosaccharide chain linked to ceramide characterizes the large family of glycosphingolipids to which gangliosides belong. The sphingolipids are classified in two subgroups, based on the carbohydrate immediately linked to ceramide The first and smaller subgroup derives from galactosylceramide.

Most of the glycosphingolipids, and thus virtually all gangliosides, belong to the subgroup derived from glucosylceramide.

4. Sialic acid is present in brain gangliosides mainly in the N-acetyl form, but in some ganglioside species the N-glycolyl form has been identified. This residue is generally termed neuraminic acid (NANA or NGNA).

FIG. 2: N-acetylneuraminic acid; open chain and hemiketalic ring.

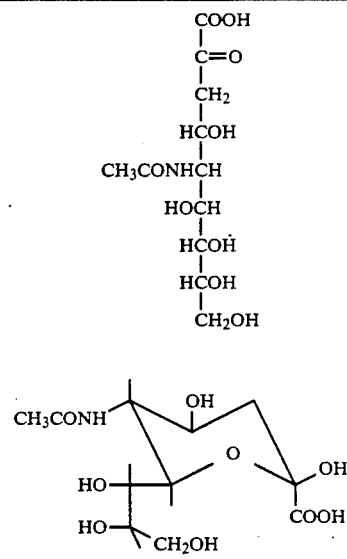

The hydrophilicity of gangliosides is due to the oligosaccharide chain and to the number of sialosyl residues linked to this chain.

Distribution of Gangliosides

The highest concentration of gangliosides is found in cerebral grey matter, which contains approximately 2.5 micromoles of NANA per gram wet weight (approximately 0.4% of dry weight, 0.6% of total lipids) (Ledeen R., Salsmar K., Cabrera M., J. Lipid Res.: 9, 129 (1968)).

About 90% of the total ganglioside content of mammalian brain is comprised of four gangliosides having an identical oligosaccharide sequence:

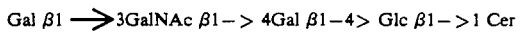

Gal β1 →3GalNAc β1–> 4Gal β1–4> Glc β1–>1 Cer

Most of the remaining 10% mammalian brain ganglioside content is comprised of gangliosides lacking the terminal galactose or the galactosyl-Nacetylgalactosamine unit (Syennerholm L., Mansson S., Li Y., J. Biol. Chem. 248: 740 (1973)).

Structure and Nomenclature of Gangliosides

Brain gangliosides have been isolated and purified by chromatographic procedures. The structure of ganglioside GM$_1$ was determined first and was shown to be common to the four main gangliosides present in mammalian brain. A summarizing structure description is given in Table 1, which is followed by detailed single description of the four main mammalian brain gangliosides:

SUMMARIZING TABLE OF GANGLIOSIDE STRUCTURE

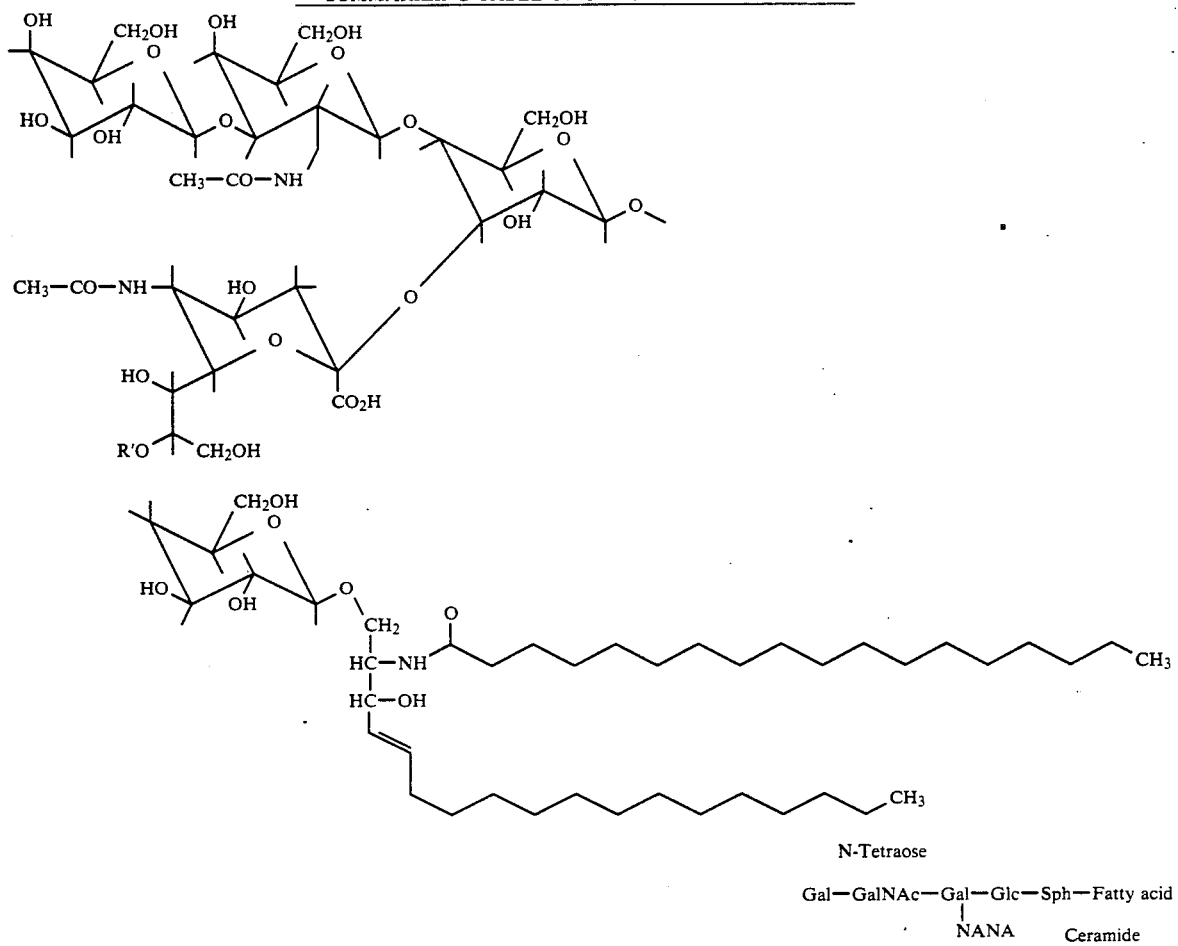

N-Tetraose

Gal—GalNAc—Gal—Glc—Sph—Fatty acid
            |
            NANA        Ceramide

TABLE 1
Structures of Four Main Mammalian Brain Gangliosides

| Symbol according to Svennerholm* | Abbreviation according to IUPAC-IUB | R | R' |
|---|---|---|---|
| $GM_1$ | $II^3\alpha$-NeuAc-GgOse$_4$Cer | H | H |
| $GD_{1a}$ | $II^3\alpha$-NeuAc-$IV^3$-$\alpha$-NeuAc-GgOse$_4$Cer | NANA | H |
| $GD_{1b}$ | $II^3\alpha$-(NeuAc)$_2$GgOse$_4$Cer | H | NANA |
| $GT_{1b}$ | $II^3\alpha$-(NeuAc)$_2$-$IV^3$-$\alpha$-NeuAc-GgOse$_4$Cer | NANA | NANA |

*(Svennerholm L., J. Neurochem. 10: 613 (1963))

1. Ganglioside $GM_1$

Ganglioside $GM_1$ has the simplest structure of the four main gangliosides; the others ($GD_{1a}$, $GD_{1b}$, $GT_{1b}$) are identical but for the addition of one or more sialosyl residues attached by glyscosidic linkages to the oligosaccharide moiety.

1.1 Structure

Gal $\beta 1 \rightarrow$ 3GalNAc $\beta 1 \rightarrow$ 4Gal(3 $\leftarrow$ 2NeuAc)$\beta 1 \rightarrow$ 4Glc $\beta 1 \rightarrow$ 1'Cer Substituents on the root oligosaccharide are given at the beginning of the name by a Roman numeral that indicates the monosaccharide residue (counting from ceramide) on which the substitutuent is located. A superscript arabic numeral indicates the position of the glycosidic linkage.

1.2. Empirical formula (Kuhn R., Wiegandt H. (1963): Chem. Ber. 96, 866) $C_{13}H_{131}N_3O_{31}$ 1.3 Molecular weight 1536.9, calculated on the basis of 2 Gal, 1 Glc,, 1 NANA, 1 GalNAc, 1 Sphingosine ($C_{18:1}$), 1 Stearic acid.

2. Ganglioside $GD_{1a}$ 2.1. Structure

NeuAc$\alpha 2 \rightarrow$ 3Gal $\beta 1 >$ 3GalNAc$\beta 1 \rightarrow$ 4Gal(3 $\leftarrow$ 2$\alpha$NeuAc) $\beta 1 \rightarrow$ 4Glc$\beta 1 \rightarrow$ 1'Cer 2.2 Empirical formula (Kuhn R., Wiegandt H. (1963): Chem. Ber. 96, 866) $C_{84}H_{148}N_4O_{39}$ 2.3. Molecular weight 1838.0, calculated on the basis of 2 Gal,1 Glc, 2 NANA, 1 GalNAc, 1 Sphingosine ($C_{18:1}$), 1 Stearic acid.

3. Ganglioside $GD_{1b}$ 3.1. Structure

Gal $\beta 1 \rightarrow$ 3GalNAc$\beta 1 \rightarrow$ 4Gal(3 $\leftarrow$ 2$\alpha$NeuAc8 $\leftarrow$ 2$\alpha$NeuAc) $\beta 1 \rightarrow$ 4Glc$\beta 1 \rightarrow$ 1'Cer 3.2. Empirical formula (Kuhn R., Wiegandt H. (1963): Chem. Ber. 96, 866) $C_{84}H_{148}N_4O_{39}$ 3.3 Molecular weight 1838.0, calculated on the basis of 2 Gal, 1 Glc, 2 NANA, 1 GalNAc, 1 Sphingosine ($C_{18:1}$), 1 Stearic acid.

4.1. Structure

NeuAc$\alpha$2—> 3Gal $\beta$1>3GalNac$\beta$1—> 4Gal(3<—2$\alpha$NeuAc8<—2$\alpha$NeuAc)$\beta$1—> 4Glc$\beta$1—> 1'Cer 4.2 Empirical formula (Kuhn R., Wiegandt H. (1963): Chem. Ber. 96, 866) $C_{95}H_{165}N_5O_{47}$ 4.3. Molecular weight 2129.4, calculated on the basis of 2 Gal, 3 NANA, 1 GalNAc, 1 Sphingosine (C18 1), 1 Stearic acid.

It has now been found that administration of gangliosides is useful and effective in the treatment of Chagas' disease. In particular, a mixture of gangliosides $GM_1$, $GD_{1a}$, $GD_{1b}$ and $GT_{1b}$ has been found useful.

Method of Preparation

The individual ganglioside components comprising the composition of the invention can be extracted by various per se known procedures. For example, bovine brain cortex (nervous tissue) drawn from the animal is homogenized in phosphate buffer at pH 6.8. Six (6) volumes of tetrahydrofuran are then added and the resulting mixture is centrifuged. The supernatant or overfloating fraction is twice re-extracted with tetrahydrofuran. After centrifugation, the non-polar or apolar materials are removed by fractioning with ethyl ether and the aqueous tetrahydrofuran phase is introduced into an ion exchange column balanced with 50% ethanol. Ethanol (50%) is used as the eluent. To the effluent from the column is added barium hydroxide and four volumes of icy ethanol. After 18 hours under cold conditions, a precipitate is collected and then a slight amount of hydrochloric acid is added following solution in water. This solution is then dialyzed and lyophilized. The yield is now about 0.6 mg crude gangliosides per gram of nervous tissue being used.

The lyophilized powder is dispersed in 20 volumes chloroform-methanol (2:1); the solution is filtered to complete clearness and fractioned by adding 0.2 volumes potassium chloride solution in water (0.88%). The upper phase is separated, dialyzed and lyophilized. The final yield is about 0.3 mg gangliosides per gram of nervous tissue.

When separating the individual gangliosidic fractions, columns of silicid acid eluted with methanol-chloroform mixtures are utilized. Prior to use for human therapeutic application, assays should be carried out on the material obtained, such as assays relating to the absence of pyrogenic activity, proteins, anaphyllactogenic activity and histamine.

Pharmaceutical Compositions

For the novel therapeutic application according to the invention, a formulation of the ganglioside mixture should contain the individual gangliosides in the following ratios:

| Individual Ganglioside | Percent by Weight |
| --- | --- |
| $GM_1$ | about 17 to 25, preferably 19 to 23 |
| $GD_{1a}$ | about 36 to 46, preferably 36 to 44 |
| $GD_{1b}$ | about 12 to 18, preferably 14 to 18 |
| $GT_{1b}$ | about 14 to 22, preferably 17 to 21 |
| $GD_3$ | about 1.0 to 2.5 |
| $GQ_{1b}$ | about 1.0 to 2.5 |

In a particularly preferred formulation, the individual gangliosides are combined in the following average weight ratio:
$GM_1$—21%
$GD_{1a}$—40%
$GD_{1b}$—16%
$GT_{1b}$—19%
$GD_3$13 2%
$GQ_{1b}$—2%

The compositions useful in the present invention may also contain small or minor amounts of other related gangliosides. For example, a composition may additionally contain from 1.0 to 2.5 weight percent of $GD_3$ and/or from 1.0 to 2.5% of $GQ_{1b}$.

In preparing a pharmaceutical composition according to the invention, the formulation should preferably contain a total ($GM_1+GD_{1a}+GD_{1b}+GT_{1b}$) ganglioside titer of $\geqq 95.0\%$ (calculated with reference to dry weight). The preparations can be solutions of the ganglioside compounds or a lypholized powder of the compounds in association with one or more pharmaceutically acceptable carriers or diluents, and contained in buffered media at a suitable pH and is osmotic with physiological fluids. Each dose of the mixture will contain from about 10 to 100 mg of the ganglioside mixture or of the single ganglioside fractions or their binary or tertiary mixtures thereof. The particular dosage will depend upon the desired effect and upon the administration route. For example, the dosage can be between 0.143 and 1.43 mg of the active compounds per kg of body weight by day with a unitary dosage of between 10 and 100 mg/by day. Preferred administration comprises a regimen of 40 mg of the ganglioside mixture in 2 ml solution, IM every day for 8 weeks.

Some possible pharmaceutical compositions are as follows:

| Preparation No. 1 - one ml vial contains: | |
| --- | --- |
| ganglioside mixture of ratio: | 100 mg |
| $GM_1$ 21% | |
| $GD_{1a}$ 40% | |
| $GD_{1b}$ 16% | |
| $GT_{1b}$ 19% | |
| phosphate buffer pH 7.6M/100 in apyrogenic sterile bidistilled water q.s.a. | 2 ml |
| Preparation No. 2 - one 2 ml vial contains: | |
| ganglioside mixture of ratio: | 10 mg |
| $GM_1$ 21% | |
| $GD_{1a}$ 40% | |
| $GD_{1b}$ 16% | |
| $GT_{1b}$ 19% | |
| phosphate buffer pH 7.6M/100 in apyrogenic sterile bidistilled water q.s.a. | 2 ml |
| Preparation No. 3 - one 2 ml vial contains: | |
| ganglioside mixture of ratio: | 25 mg |
| $GM_1$ 25% | |
| $GD_{1a}$ 40% | |
| $GD_{1b}$ 16% | |
| $GT_{1b}$ 19% | |
| phosphate buffer pH 7.6M/100 in apyro- | 2 ml |

-continued

| | |
|---|---|
| genic sterile bidistilled water q.s.a. | |
| Preparation No. 4 - one 2 ml vial contains: | |
| ganglioside mixture of ratio:<br>$GM_1$ 25%<br>$GD_{1a}$ 40%<br>$GD_{1b}$ 16%<br>$GT_{1b}$ 19% | 75 mg |
| phosphate buffer pH 7.6M/100 in apyrogenic sterile bidistilled water q.s.a. | 2 ml |
| Preparation No. 5 - one 2 ml vial contains: | |
| ganglioside mixture of ratio:<br>$GM_1$ 21%<br>$GD_{1a}$ 40%<br>$GD_{1b}$ 16%<br>$GT_{1b}$ 19%<br>$GD_3$ 2%<br>$GQ_{1b}$ 2% | 40 mg |
| phosphate buffer pH 7.6M/100 in apyrogenic sterile bidistilled water q.s.a. | 2 ml |
| Preparation No. 6 -<br>Each freeze-dried vial contains: | |
| ganglioside mixture in the proportions:<br>$GM_1$ 21%<br>$GD_{1a}$ 40%<br>$GD_{1b}$ 16%<br>$GT_{1b}$ 19% | 75 mg |
| phosphate buffer pH 7.6M/100 in apyrogenic sterile bidistilled water q.s.a. | 2 ml |
| One 2 ml vial of solvent contains: | |
| mannitol | 25 mg |
| phosphate buffer pH 7.6M/100 in apyrogenic, sterile. distilled water q.s.a. | 2 ml |

For the treatment of the above pathologies, the gangliosides can be prepared in formulations such as ampoules, vials, plasters or creams duly prepared in combination with a pharmaceutically acceptable carrier, diluent or excipient.

These formulations, as appropriate, can be administered to a patient by various administration routes, including subcutaneous, intramuscular, intravenous, topical, inuction, transcutaneous and transdermal. For example, the active ganglioside compounds can be formulated as a mixture with an appropriate excipient and prepared in a patch form which is then applied directly to the skin, whereby the compounds pass through the skin into the patient.

The preferred ganglioside composition used for the present invention is commercially available as Cronnasial®, Fidia S.p.A., Abano Terme, Italy.

Pharmacological Properties

Neuronal destruction and abnormal autonomic system testing have been reported in Chagas' disease as described above. With this in mind, the applicants postulated that treatment with an agent capable of inducing neuronal regeneration may benefit chagasic patients by promoting neuronal repair and facilitating normalization of autonomic nervous system function. Patients with Chagas' disease who demonstrated autonomic nervous system dysfunction as evidenced by abnormal Cough/Heart Rate Response testing were selected as measured by Wei, Jy and Harris, Ws (Heart rate response to cough, J. Appl. Physiol. 53. 1039, 1982) and Wei, Jy et al. (Post-cough heart rate response; Influence of age, sex and basal blood pressure, Am. J. Physiol. 245, R18, 1983). Chagas I group (n=10) consisted of asymptomatic patients with positive *T. cruzi* serologies, normal ECG and normal CXR. Chagas II group (n=13) consisted of patients with positive *T. cruzi* serologies, abnormal ECG (e.g. right bundle branch block, left anterior hemiblock, and/or arrhythmias) and normal CXR. A Control group (n=20) was composed of patients with negative *T. cruzi* serologies and no significant medical problems. Pre-therapy baseline determinations of autonomic nervous system function by the Cough/Heart Rate Response test indicated that patients in Chagas I and Chagas II groups had a statistically significantly attenuated increase in heart rate elicited by coughing mechanism (see the results in Table 1).

Patients in both the Chagas I and Chagas II groups were then treated with Cronassial®, 10 mg, intramuscularly (IM) every day for a total of 30 days. Autonomic nervous system testing was repeated. Surprisingly, patients in the Chagas I group normalized their Cough/Heart Rate Response testing (Table 1) and patients in Chagas II group showed a significant improvement in response (Table 1). No toxicity of therapy was noted in any of the patients.

In a parallel study, autonomic nervous system function was measured by means of the Tilt test Robinson, BJ, et al. (Do elderly patients with an excessive fall in blood pressure on standing have evidence of autonomic failure? Clin. Sci, 64; 587, 1983). A third group of chagasic patient was included (Chagas III: n=15) who had positive *T. cruzi* serologies, abnormal ECG, and clinical or daiogrphic evident of cardiomegaly and/or congestive heart failure. Prior to therapy all three Chagas groups demonstrated abnormal responses to postural changes as indicted by a fall in diastolic blood pressure (Table 2).

TABLE 1

Cough/Heart Rate Response Before and After Ganglioside Therapy

| | Control | Chagas I | Chagas II |
|---|---|---|---|
| Before Ganglioside Therapy | | | |
| Basal Rate Heart Beat | 67.3 ± 10.87 | 71.5 ± 8.20 | 60.5 ± 6.00 |
| 1 | 103.4 ± 11.66 | 73.0 ± 9.50 | 64.3 ± 4.44 |
| 5 | 92.0 ± 18.14 | 74.6 ± 8.54 | 63.6 ± 7.37 |
| 10 | 79.3 ± 13.64 | 71.8 ± 9.97 | 63.7 ± 4.77 |
| 15 | 71.8 ± 10.75 | 74.5 ± 11.18 | 63.1 ± 7.25 |
| 20 | 70.5 ± 12.93 | 71.4 ± 7.24 | 60.1 ± 8.50 |
| After Ganglioside Therapy | | | |
| Basal Rate Heart Beat | | 74.3 ± 9.58 | 65.5 ± 9.77 |
| 1 | | 99.5 ± 10.35 | 88.3 ± 14.60 |
| 5 | | 90.3 ± 11.42 | 81.3 ± 18.70 |
| 10 | | 79.2 ± 11.25 | 72.5 ± 13.00 |
| 15 | | 75.0 ± 9.11 | 68.9 ± 9.12 |
| 20 | | 72.5 ± 10.34 | 66.5 ± 9.34 |

TABLE 2

Absolute Change in Diastolic Blood Pressure in mmHg as Determined by Tilt Test Ganglioside Therapy

| | Before | After |
|---|---|---|
| Control | +17.5 ± 6.3 | not done |
| Chagas I | −7.1 ± 3.9 | +10.0 ± 5.0 |
| Chagas II | −2.9 ± 5.6 | +14.6 ± 3.9 |
| Chagas III | −7.6 ± 6.0 | +13.6 ± 6.6 |

After an analogous ganglioside therapy protocol as that used in the trial described above, repeat Tilt testing revealed a normalization of response (Table 2). Chagas III patients also reported a subjective improvement after ganglioside therapy.

These studies show the beneficial effects of ganglioside therapy in correcting the autonomic nervous system abnormalities that are seen in Chagas' disease and provide a means of treatment for a disease that has been refractory to medical intervention.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. A method for the treatment of autonomic nervous system abnormalities caused by Chagas' disease or American trypanosomiasis which comprises administering to a patient in need thereof a therapeutically effective amount of a pharmaceutical composition which comprises a mixture of gangliosides $GM_1$, $GM_{1a}$, $GD_{1b}$ and $GT_{1b}$.

2. The method according to claim 1, wherein said administration induces neuronal regeneration, promotes neuronal repair and facilitates normalization of the autonomic nervous system functions in said patient.

3. The method according to claim 1, wherein said composition comprises 17 to 25% by weight of $GM_1$, 36 to 46% by weight of $GD_{1a}$, 12 to 18% by weight of $GD_{1b}$ and 14 to 22% by weight of $GT_{1b}$.

4. The method according to claim 3, wherein said composition additionally contains 1.0 to 2.5% $GD_3$ and 1.0 to 2.5% $GQ_{1b}$.

5. The method according to claim 3, wherein said composition comprising 21% $GM_1$, 40% $GD_{1a}$, 16% $GD_{1b}$ 19% $GT_{1b}$, 2% $GD_3$ and 2% $GQ_{1b}$.

6. The method according to any one of claims 1, 2, 3, 4 or 5 wherein said gangliosides are administered at a rate of 10 to 100 mg/by day.

7. The method according to claim 6, wherein said gangliosides are administered daily at a rate of 40 mg per patient.

8. A method for the treatment of autonomic nervous system abnormalities caused by Chagas' disease or American trypanosomiasis which comprises administering to a patient in need of such treatment between 10 to 100 mg per day of a pharmaceutical composition which comprises about 17 to 25% by weight of ganglioside $GM_1$, about 36 to 46% by weight of ganglioside $GD_{1a}$, about 12 to 18% by weight of ganglioside $GD_{1b}$, and about 14 to 22% by weight of $GT_{1b}$.

9. The method according to claim 8, wherein said composition comprises about 12% $GM_1$, about 40% $GD_{1a}$, about 16% $GD_{1b}$ and about 19% $GT_{1b}$.

10. The method according to claim 9, wherein said composition additionally contains about 2% $GD_3$ and about 2% $GQ_{1b}$.

* * * * *